(12) United States Patent
Jiang et al.

(10) Patent No.: US 8,268,146 B2
(45) Date of Patent: *Sep. 18, 2012

(54) MEASUREMENT OF HYDROGEN SULPHIDE AND THIOLS IN FLUIDS

(75) Inventors: Li Jiang, Newton, MA (US); Timothy Gareth John Jones, Cambridgeshire (GB); Jonathan Webster Brown, Aberdeen (GB); Andrew Gilbert, Aberdeenshire (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 8 days.

This patent is subject to a terminal disclaimer.

(21) Appl. No.: 12/797,148

(22) Filed: Jun. 9, 2010

(65) Prior Publication Data
US 2010/0243480 A1     Sep. 30, 2010

Related U.S. Application Data

(63) Continuation of application No. 10/541,568, filed as application No. PCT/GB03/02345 on May 28, 2003, now Pat. No. 7,758,734.

(30) Foreign Application Priority Data

Jan. 15, 2003    (GB) .................................. 0300812.5

(51) Int. Cl.
*G01N 27/26* (2006.01)
*G01N 27/30* (2006.01)
*G01N 27/333* (2006.01)
*G01N 27/407* (2006.01)

(52) U.S. Cl. ........ 204/409; 204/412; 204/406; 204/415; 204/418; 204/419; 204/424; 204/431; 204/434; 436/121; 436/25; 436/30; 436/32; 422/82.03; 205/786.5; 205/775

(58) Field of Classification Search .................. 204/409, 204/412, 406, 415, 418, 419, 424, 431, 434; 436/121, 25, 30, 32; 422/82.03; 205/786.5, 205/775
See application file for complete search history.

(56) References Cited

U.S. PATENT DOCUMENTS
3,780,575 A    12/1973   Urbanosky
(Continued)

FOREIGN PATENT DOCUMENTS
DE           275924 A1     2/1990
(Continued)

OTHER PUBLICATIONS

Lawrence et al, "The electrochemical analog of the methylene blue reaction: a novel amperometric approach to the detection of hydrogen sulfide", Electroanalysis 2000, vol. 12, No. 18, pp. 1453-1460.

(Continued)

*Primary Examiner* — Bruce Bell

(57) ABSTRACT

A wellbore tool has an electrochemical sensor for measuring the amount of hydrogen sulphide or thiols in a fluid downhole in a wellbore. The sensor comprises a temperature- and pressure-resistant housing containing a flow path for the fluids. The fluids flow over one side of a gas permeable membrane the other side of the membrane being exposed to a chamber containing at least two electrodes and containing a reaction solution which together with the hydrogen sulphide or thiols create a redox reaction resulting in an electrical current dependent upon the amount of hydrogen sulphide or thiols in the fluid. Measurement is made by passing formation fluid along the flow path and repeatedly applying varying potential to one electrode and measuring the peak current flowing between that electrode and a second electrode.

28 Claims, 8 Drawing Sheets

U.S. PATENT DOCUMENTS

| | | | |
|---|---|---|---|
| 3,859,851 A | | 1/1975 | Urbanosky |
| 3,915,831 A | | 10/1975 | Riseman et al. |
| 3,988,233 A | | 10/1976 | Gamer et al. |
| 4,490,234 A | | 12/1984 | Buzza |
| 4,699,892 A | | 10/1987 | Suzuki |
| 4,994,671 A | | 2/1991 | Safinya et al. |
| 5,480,808 A | * | 1/1996 | Kauffman et al. ............ 436/135 |
| 5,499,528 A | | 3/1996 | Bahar |
| 5,624,546 A | | 4/1997 | Milco |
| 5,667,558 A | | 9/1997 | Bryan et al. |
| 6,584,827 B2 | | 7/2003 | Kiesele et al. |
| 6,629,444 B2 | | 10/2003 | Peng |
| 6,939,717 B2 | * | 9/2005 | Jiang et al. .................... 436/121 |
| 7,407,566 B2 | * | 8/2008 | Jiang et al. .................... 204/400 |
| 7,520,160 B1 | * | 4/2009 | Toribio et al. ................ 73/31.05 |
| 7,758,734 B2 | * | 7/2010 | Jiang et al. .................... 204/409 |

FOREIGN PATENT DOCUMENTS

| | | |
|---|---|---|
| EP | 0629854 A | 12/1994 |
| GB | 2359631 B | 3/2002 |
| GB | 2397651 B | 8/2005 |
| GB | 2391314 B | 10/2005 |
| WO | 0163094 A1 | 8/2001 |
| WO | 2004011929 A1 | 5/2004 |

OTHER PUBLICATIONS

Lawrence et al, "Amperometric detection of sulfide at a boron doped diamond electrode: the electrocatalytic reaction of sulfide with ferricyanide in aqueous solution", Electroanalysis 2002, 14, No. 7-8, pp. 499-504.

Harold Rhodes, "Determination of hydrogen sulfide content in natural gas, evaluation of containers for preparation of calibration standards, and sample collection procedure", Report of Investigations No. 8391, U.S. Department of the Interior, Bureau of Mines, 1979, 16 pages.

Schlumberger, "Wireline Formation Testing and Sampling", Houston, 1996, pp. 10-1 to 10-25.

* cited by examiner

MEASUREMENT OF HYDROGEN SULPHIDE AND THIOLS IN FLUIDS

RELATED APPLICATIONS

This application is a continuation of U.S. application Ser. No. 10/541,568 which is incorporated herein by reference and which was based on PCT application PCT/GB2003/002345 filed 28 May 2003. This application claims priority under 35 USC 119 from GB application 03/0008125.5 dated 15 Jan. 2003.

FIELD OF THE INVENTION

This invention relates to methods and apparatus for measuring the amount of hydrogen sulphide and thiols in fluids, and is more particularly but not exclusively concerned with methods and apparatus for measuring the amount of hydrogen sulphide and thiols in formation fluids from an earth formation surrounding a wellbore.

BACKGROUND OF THE INVENTION

It is highly desirable to be able to determine at as early a stage as possible the amount of hydrogen sulphide in oil and gas deposits in the earth formations surrounding a wellbore, since the amount of hydrogen sulphide can seriously impact the economic value of the deposits, and affect the composition (and therefore the cost) of the metalwork used in the extraction of the deposits from the formations. Additionally, because hydrogen sulphide is toxic in even relatively low concentrations, the hydrogen sulphide content of the deposits has an important bearing on the health, safety and environmental aspects of their extraction.

Several methods and apparatuses for the measurement of the hydrogen sulphide content of wellbore fluids are described in International Application No. WO 01/63094 (now granted as UK Patent No. 2 395 631). Among these are a method and apparatus based on an electrochemical sensor in which the current created by a redox reaction involving the hydrogen sulphide is measured. More specifically, the sensor comprises a reaction chamber or cell containing a precursor or catalyst (hereinafter referred to simply as a precursor) in an aqueous reaction solution, the walls of the chamber including a gas permeable membrane over which the wellbore fluids flow and through which hydrogen sulphide in the wellbore fluids diffuses into the reaction chamber to initiate the redox reaction, at the surface of an electrode controlled at certain voltage.

However, as the search for hydrocarbons is extended, wellbores are becoming deeper, so that the environment, in which electrochemical sensors are required to operate, is becoming increasingly hostile. Typically, the sensors need to be able to operate at temperatures of up to 200 degrees Celsius and pressures of up to 20,000 psi.

It is an object of the present invention to provide new electrochemical sensors of the type in which the current created by a redox reaction involving the hydrogen sulphide is measured, and which are suitable for use in severe borehole environments.

SUMMARY OF THE INVENTION

According to a first aspect of the present invention, there is provided an electrochemical sensor for measuring the amount of hydrogen sulphide or thiols in a fluid, the sensor comprising a housing having a flow path for the fluid therethrough, a substantially rigid gas permeable membrane disposed in the housing and having one side exposed to the flow path, and a chamber disposed in the housing, the chamber being exposed to the other side of the membrane and containing reagents which together with the hydrogen sulphide or thiols entering the chamber via the membrane create a redox reaction resulting in an electrical current dependent upon the amount of hydrogen sulphide or thiols in said fluid.

Preferably, the housing is provided with pressure balancing means for reducing the difference between the respective pressures on each side of the membrane.

It will be appreciated that the pressure balancing means serves to reduce the stresses on the membrane resulting from the generally high pressure environment in which the sensor is used, and in particular from rapid variations in pressures, which can sometimes vary between 20,000 psi and atmospheric in just a few seconds.

Advantageously, the pressure balancing means comprises a movable partition, piston or bellow having a first pressure surface in pressure communication with the flow path and a second pressure surface in pressure communication with the chamber. Thus the first pressure surface of the movable piston may be directly exposed to the fluid path, and the second pressure surface of the movable piston may be directly exposed to the reagents.

Also, the membrane is preferably trapped between respective sealing means which extend around the periphery of the membrane on each side thereof.

Advantageously, the housing includes a first housing member which is generally cup-shaped and is provided with a centrally disposed aperture in its base, and a second housing member which is substantially cylindrical and screws coaxially into the cup-shaped housing member so as to trap the membrane between the end of the second housing member within the first housing member and the base of the cup shape of the first housing member, one side of the membrane completely covering said aperture, and the flow path extending transversely through both housing members and communicating with the other side of the membrane via a coaxially disposed conduit in the second housing member. Conveniently, the housing includes a third housing member having a generally cylindrical recess for coaxially receiving the first and second housing members so as to define therewith a cylindrical space between the base of the cup shape of the first housing member and the base of the recess, said cylindrical space forming at least part of the chamber. The sealing means on said one side of the membrane preferably comprises a substantially coaxially disposed O-ring trapped between said one side of the membrane and the base of the cup shape of the first housing member, while the sealing means on the other side of the membrane may comprise sealing engagement between said other side of the membrane and a planar surface formed on the end of the second housing member within the first housing member. A further coaxially disposed O-ring may be trapped between the base of the cup shape of the first housing member and the base of the recess.

The chamber preferably includes a working electrode, a counter electrode and a reference electrode, the electrodes being spaced apart in the chamber and arranged such that said current flows between the working and counter electrodes. Advantageously, the working electrode is made from boron-doped diamond, although it can also be made from glassy carbon or platinum.

The chamber is exposed to the other side of the membrane and contains a working electrode, a counter electrode, a reference electrode and reagents which together with the hydrogen sulphide or thiols entering the chamber via the membrane create the redox reaction resulting in the electrical current dependent upon the amount of hydrogen sulphide or thiols in the fluid between the working and counter electrodes, wherein the working electrode is made from boron-doped diamond, glassy carbon or platinum.

The counter electrode may be made of platinum, while the reference electrode may be made of silver coated with silver chloride or silver iodide, or platinum. The electrodes may be mounted on or in an insulating base, preferably made from polyetheretherketone (PEEK). The housing members may also be made from PEEK. The reagents may include dimethylphenylenediamine (DMPD) or its structural analogues, or an aqueous ferrocyanide or ferrocene solution. The membrane may be made from zeolite or a suitable ceramic material.

From another aspect, the invention also includes a method of measuring the amount of hydrogen sulphide or thiols in formation fluid from an earth formation surrounding a wellbore, the method comprising positioning a wellbore tool equipped with an electrochemical sensor in accordance with the first aspect of the invention in the wellbore adjacent to the formation, exposing the sensor to the formation fluid, and measuring the resulting redox current produced by the sensor.

BRIEF DESCRIPTION OF THE DRAWINGS

The invention will now be described, by way of example only, with reference to the accompanying drawings, of which.

Figure 1:
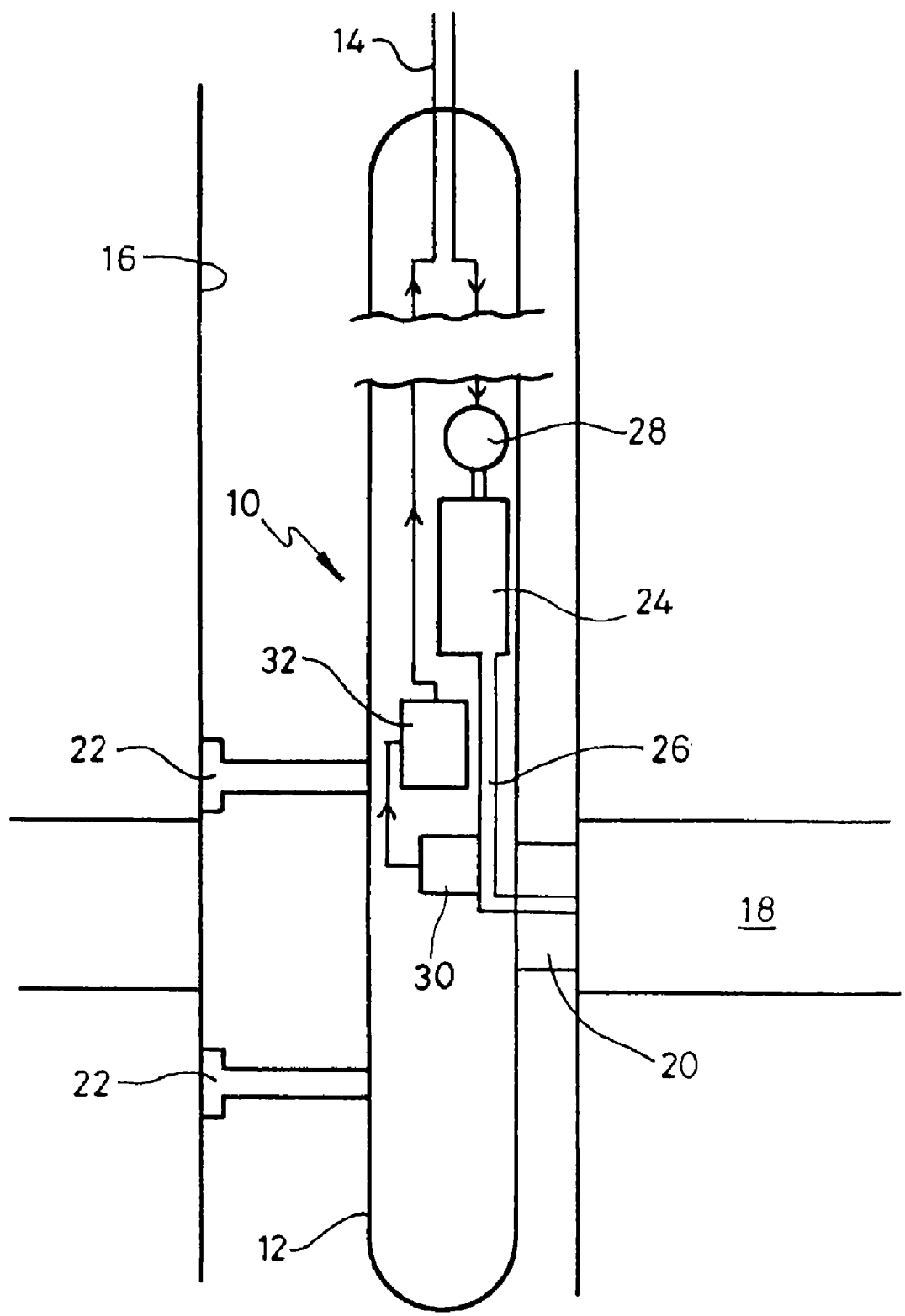
FIG. 1 is a schematic representation of a wellbore tool which is positioned in a wellbore and which is equipped with an electrochemical sensor in accordance with the present invention for measuring the amount of hydrogen sulphide or thiols in formation fluid from an earth formation surrounding the wellbore.

The terms "upper" and "lower" used in relation to the embodiments of the sensor of the invention described below merely refer to the orientation of the sensor as viewed in the drawings, and have no significance to the orientation of the sensor in use or any other context.

DETAILED DESCRIPTION OF THE INVENTION

The wellbore tool shown in FIG. 1 is indicated at 10, and is based on Schlumberger's well known modular dynamics tester (MDT), as described in Trans. SPWLA 34$^{th}$ Annual Logging Symposium, Calgary, Jun. 1993, Paper ZZ and in U.S. Pat. Nos. 3,780,575, 3,859,851 and 4,994,671. The tool 10 comprises an elongate substantially cylindrical body 12, which is suspended on a wireline 14 in the wellbore, indicated at 16, adjacent an earth formation 18 believed to contain recoverable hydrocarbons, and which is provided with a radially projecting sampling probe 20. The sampling probe 20 is placed into firm contact with the formation 18 by hydraulically operated rams 22 projecting radially from the body 12 on the opposite side from the sampling probe, and is connected internally of the body to a sample chamber 24 by a conduit 26.

In use, and prior to completion of the well constituted by the wellbore 16, a pump 28 within the body 12 of the tool 10 can be used to draw a sample of the hydrocarbons into the sample chamber 24 via the conduit 26. The pump is controlled from the surface at the top of the wellbore via the wireline 14 and control circuitry (not shown) within the body 12. It will be appreciated that this control circuitry also controls valves (not shown) for selectively routing the sampled hydrocarbons either to the sample chamber 24 or to a dump outlet (not shown), but these have been omitted for the sake of simplicity.

In accordance with the present invention, the conduit 26 additionally communicates with an electrochemical sensor 30 also provided within the body 12 of the tool 10, so that the hydrocarbons flow over a face of the sensor on their way through the conduit. The sampling probe is located close to the electrochemical sensor 30, at a distance comprised between 8 and 30 cm from said electrochemical sensor, advantageously approximately equal to 15 cm. As will become apparent, the sensor 30 produces an output current, which is dependent on the amount of hydrogen sulphide or thiols in the hydrocarbons flowing through the conduit 26. This output current is measured in known manner by a digital current measuring circuit 32 in the body 12 of the tool 10, and the measurement is transmitted to the surface via the wireline 14.

The sensor 30 is shown in more detail in FIGS. 2 to 6, and comprises a generally cylindrical housing 40, which is made from polyetheretherketone (PEEK) and which comprises a main housing member 42 having an upper portion 44 (as viewed in the drawings), a reduced diameter lower portion 46, and a stepped diameter cylindrical bore 48 extending coaxially through it from top to bottom. The bore 48 has a large diameter upper portion 50 wholly within the upper portion 44 of the main housing member 42, an intermediate diameter portion 52 also wholly within the upper portion of the main housing member, and a reduced diameter portion 54 largely within the lower portion 46 of the main housing member.

A flowpath 56 for the fluid whose hydrogen sulphide content is to be sensed extends diametrically through the upper portion 44 of the main housing member 42, intersecting the upper portion 50 of the bore 48.

Figure 2:
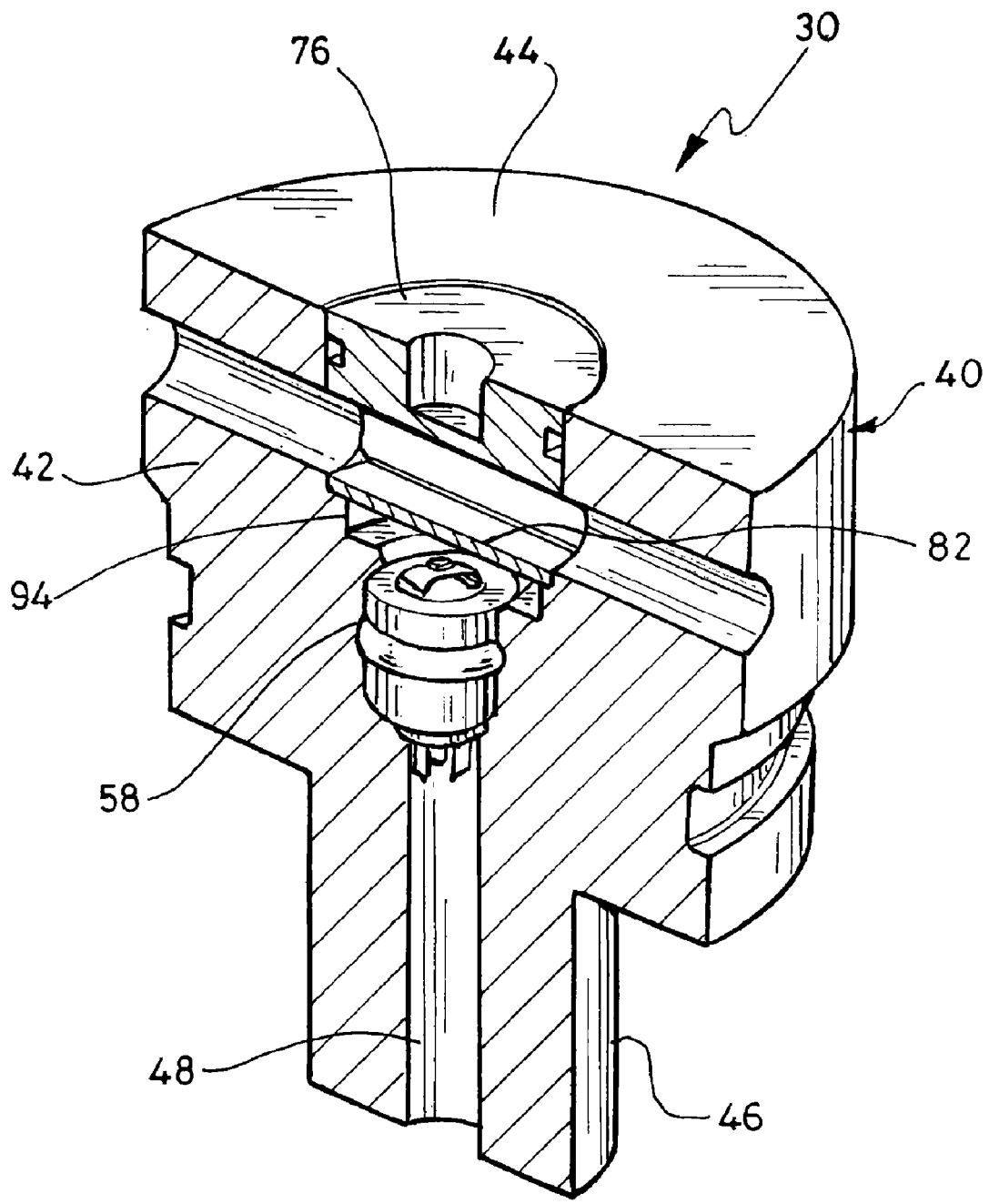
FIG. 2 is a partially cutaway perspective view of the electrochemical sensor of FIG. 1.
Figure 3:
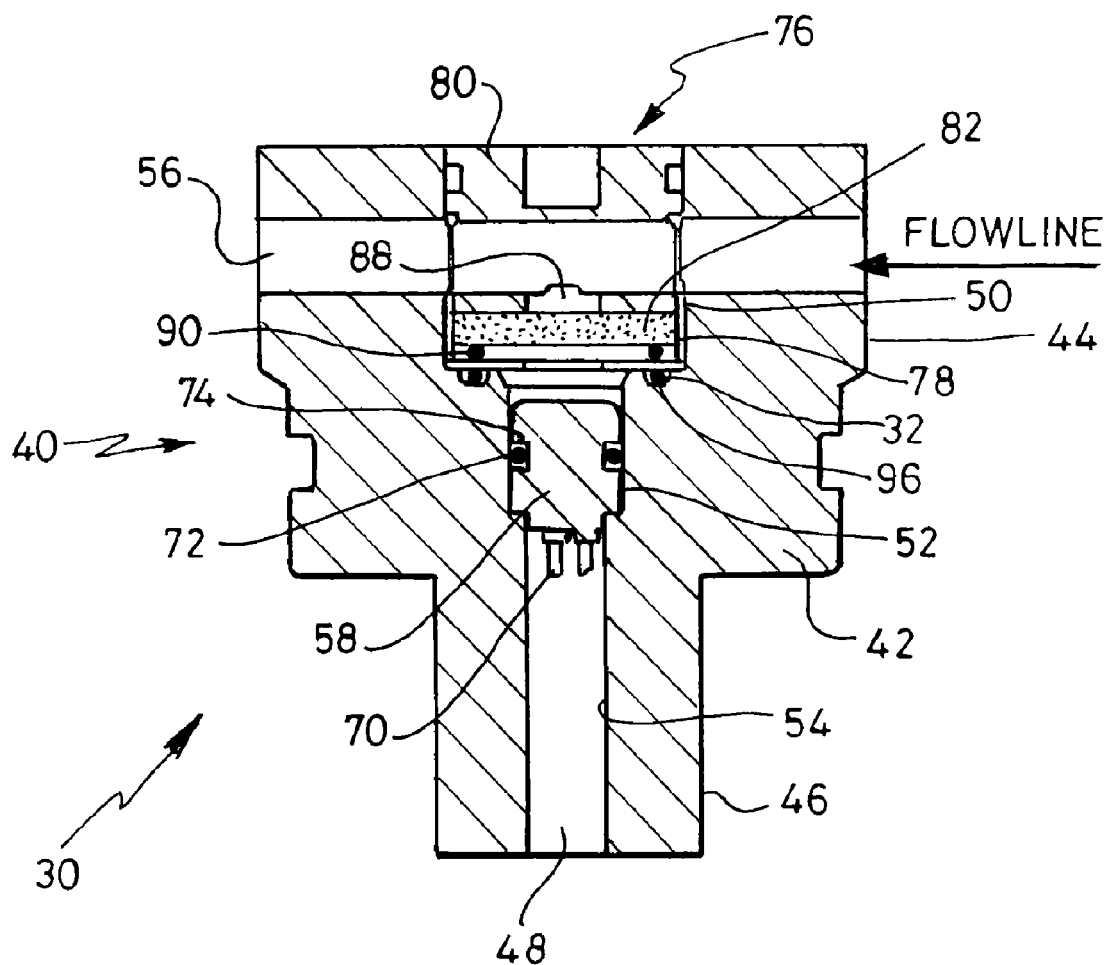
FIG. 3 is a more detailed sectional view of the electrochemical sensor of FIG. 2.
Figure 4:
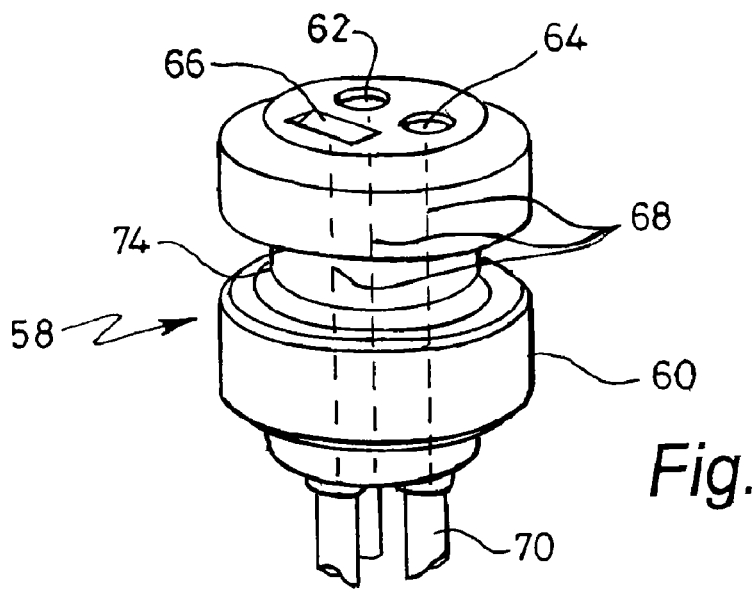
FIG. 4 shows an electrode assembly forming part of the sensor of FIGS. 2 and 3.
Figure 5A:
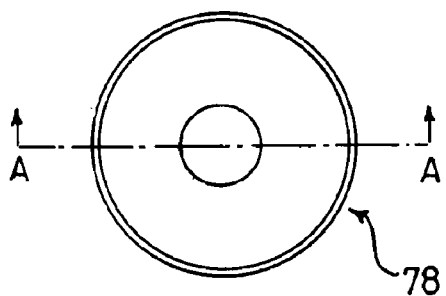
FIGS. 5A, 5B, 5C and 5D are four different views of part of the housing of the sensor of FIGS. 2 and 3.
Figure 5B:
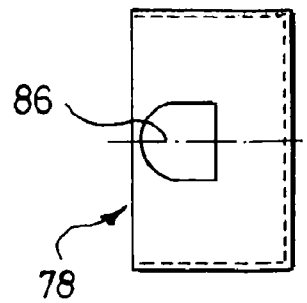
Figure 5C:
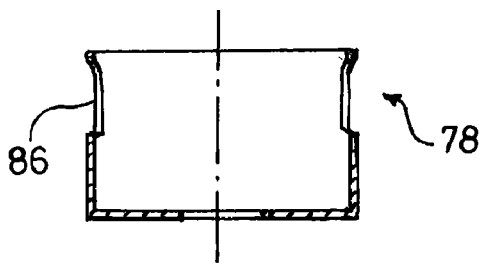
Figure 5D:
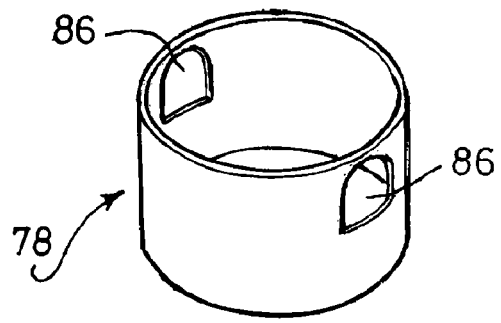
Figure 6A:
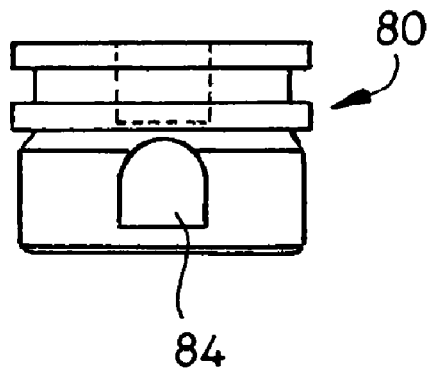
FIGS. 6A, 6B and 6C are three different views of another part of the housing of the sensor of FIGS. 2 and 3.
Figure 6B:
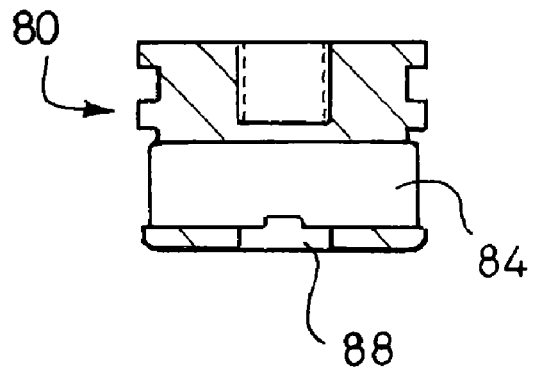
Figure 6C:
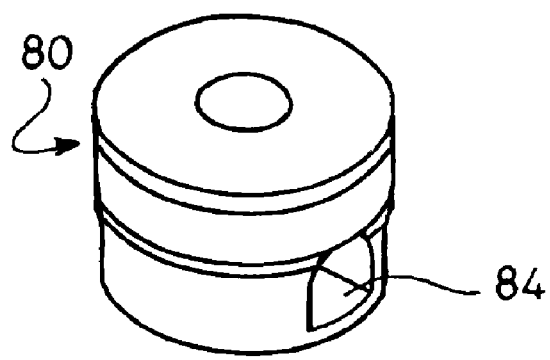

Disposed in the intermediate diameter portion 52 of the bore 48, and resting on the shoulder defined between the reduced diameter portion 54 and the intermediate diameter portion, is a cylindrical electrode assembly 58, best seen in FIGS. 2, 3 and 4. The electrode assembly 58 comprises an insulating body 60, also made of PEEK, having three electrodes on its upper surface, namely a working electrode 62 made from boron-doped diamond, a reference electrode 64 in the form of a silver dot coated with silver chloride or silver iodide, and a counter electrode 66 comprising a printed platinum track. The electrodes 62, 64, 66 are connected via respective electrical conductors 68 moulded into and extending axially through the body 60 in a sealed manner to respective electrical leads 70, which exit the main housing 30 via the reduced diameter portion 54 of the bore 48. An O ring 72 made of VITON™ is disposed in a groove 74 extending coaxially round the body 60 to seal the electrode assembly 58 within the intermediate diameter portion 52 of the bore 48.

Disposed in the large diameter upper portion 50 of the bore 48, and resting on the shoulder defined between the intermediate diameter portion 52 and the large diameter portion is a cylindrical membrane retainer assembly 76, which comprises a cup-shaped housing member 78 (best seen in FIGS. 5A, 5B, 5C and 5D), a cylindrical housing member 80 (best seen in FIGS. 6A, 6B and 6C) which screws part of the way into the cup-shaped housing member 78, and a gas permeable membrane 82 in the form of a circular plate made of zeolite or other suitable ceramic material coaxially located in the cup-shaped housing member 78, in the space between the bottom of the inside of the cup shape of the housing member 78 and the bottom of the housing member 80. The housing member 80 has a diametrically extending flow path 84 therethrough, and the housing member 78 has diametrically opposed ports 86 aligned with the opposite ends of the flow path 84, the flow path 84 and the ports 86 being aligned with the flow path 56 in the upper part 44 of the main housing member 42. The housing member 80 further includes a short duct 88 communicating between the flow path 84 and the bottom of the housing member, and therefore communicating with the upper surface of the membrane 82.

The bottom of the housing member 80 is flat, and bears on the upper surface of the membrane 82, pressing it towards the bottom of the inside of the housing member 78. An O-ring seal 90 made of VITON™ is trapped between the lower surface of the membrane 82 and the bottom of the inside of the housing member 78 to provide sealing around the entire periphery of the lower surface of the membrane, while the flat bottom of the housing member 80 and the upper surface of the membrane 82 provides a seal around the entire periphery of the upper side of the membrane. A further O-ring seal 92 also made of VITON™ is disposed in a groove 96 formed coaxially in the shoulder defined between the intermediate diameter portion 52 and the large diameter portion of the bore 48, and is trapped between the underside of the bottom of the housing member 78 and the shoulder.

The generally cylindrical space 94 beneath the underside of the membrane 82 and the top of the electrode assembly constitutes a reaction chamber, and is filled with a reaction solution containing a precursor or catalyst, for example, dimethylphenylenediamine (DMPD).

Figure 7:
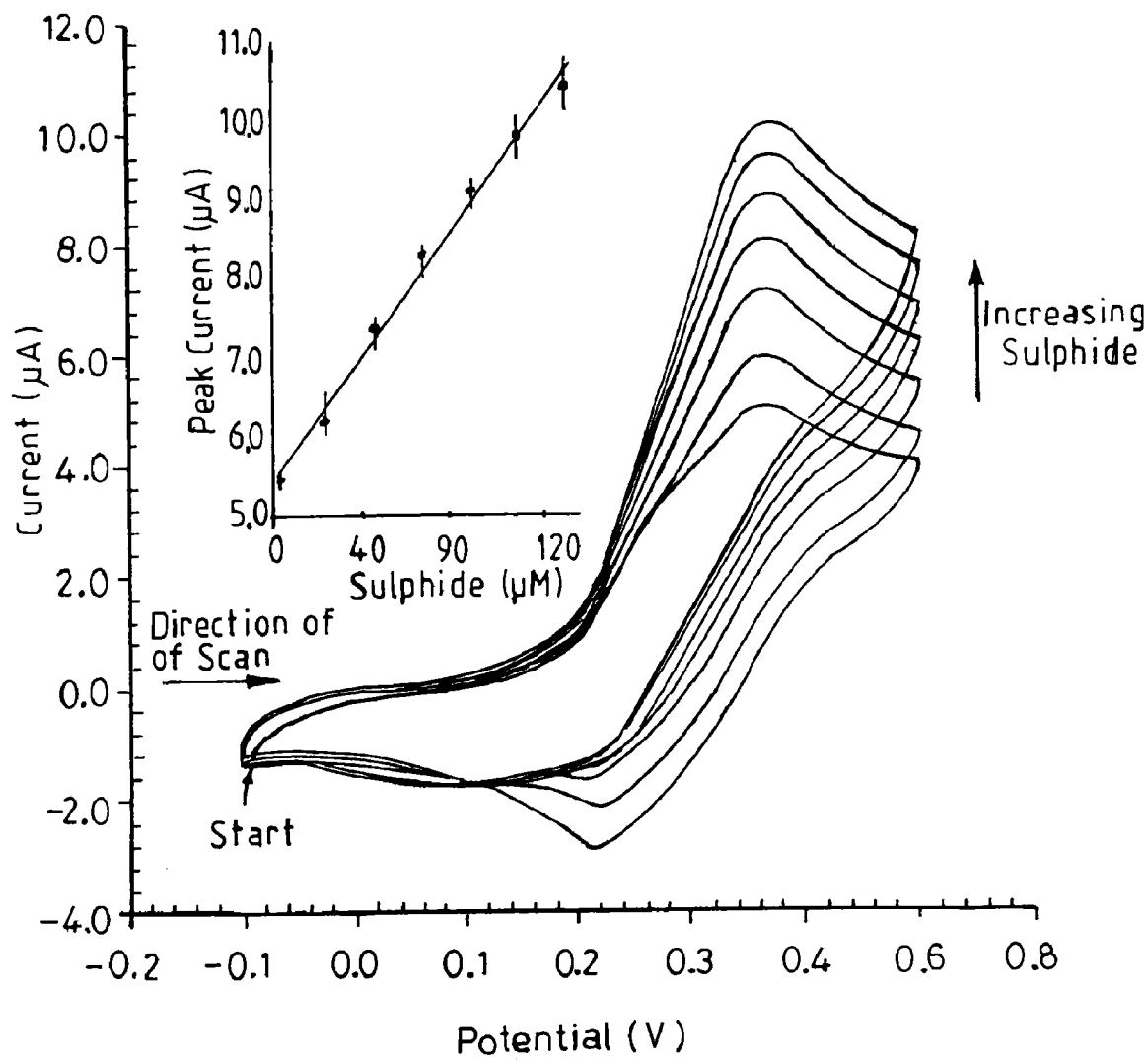
FIG. 7 shows cyclic voltammograms for the sensor of FIGS. 2 and 3 for various concentrations of hydrogen sulphide, using dimethylphenylenediamine (DMPD)

In operation, the sensor 30 fits in a cylindrical recess in a block (not shown) through which the conduit 26 passes, with the flow path 56 in alignment with the conduit 26, and with sealing provided by a VITON™ O-ring (not shown) in a groove 96 in the upper portion 44 of the housing 40 of the sensor. The upper side of the membrane 82 in the sensor 30 is thus exposed via the flow path 56 the ports 86, the flow path 84 and the duct 88 to the hydrocarbons in the conduit 26, and suitable electronic measurement equipment is used to apply a cyclically varying potential between the working electrode 40 and the reference electrode 44, and to measure the peak currents flowing between the working electrode 40 and counter electrode 42. Cyclic voltammograms for the sensor 30 are shown in FIG. 7, which includes an inset graph showing the variation of the peak oxidation current with sulphide concentration. It can be seen that for concentrations of sulphide between $20\times10^{-6}$ molar (0.7 ppm) and $100\times10^{-6}$ molar (3.5 ppm), the oxidation current increases substantially linearly with increasing sulphide concentration.

The sealing of the membrane 82 in the housing members 78 and 80 using a surface-to-surface seal and the O-ring seal 90, coupled with the sealing provided by the O-ring seal 92, ensures that the reaction solution is not washed out of the chamber 94 by the hot, high pressure hydrocarbons in the flow path 56, while the materials used, in particular for the membrane 82, are also able to withstand the hostile borehole environment.

Many modifications can be made to the described implementation of the sensor 30.

Figure 8:
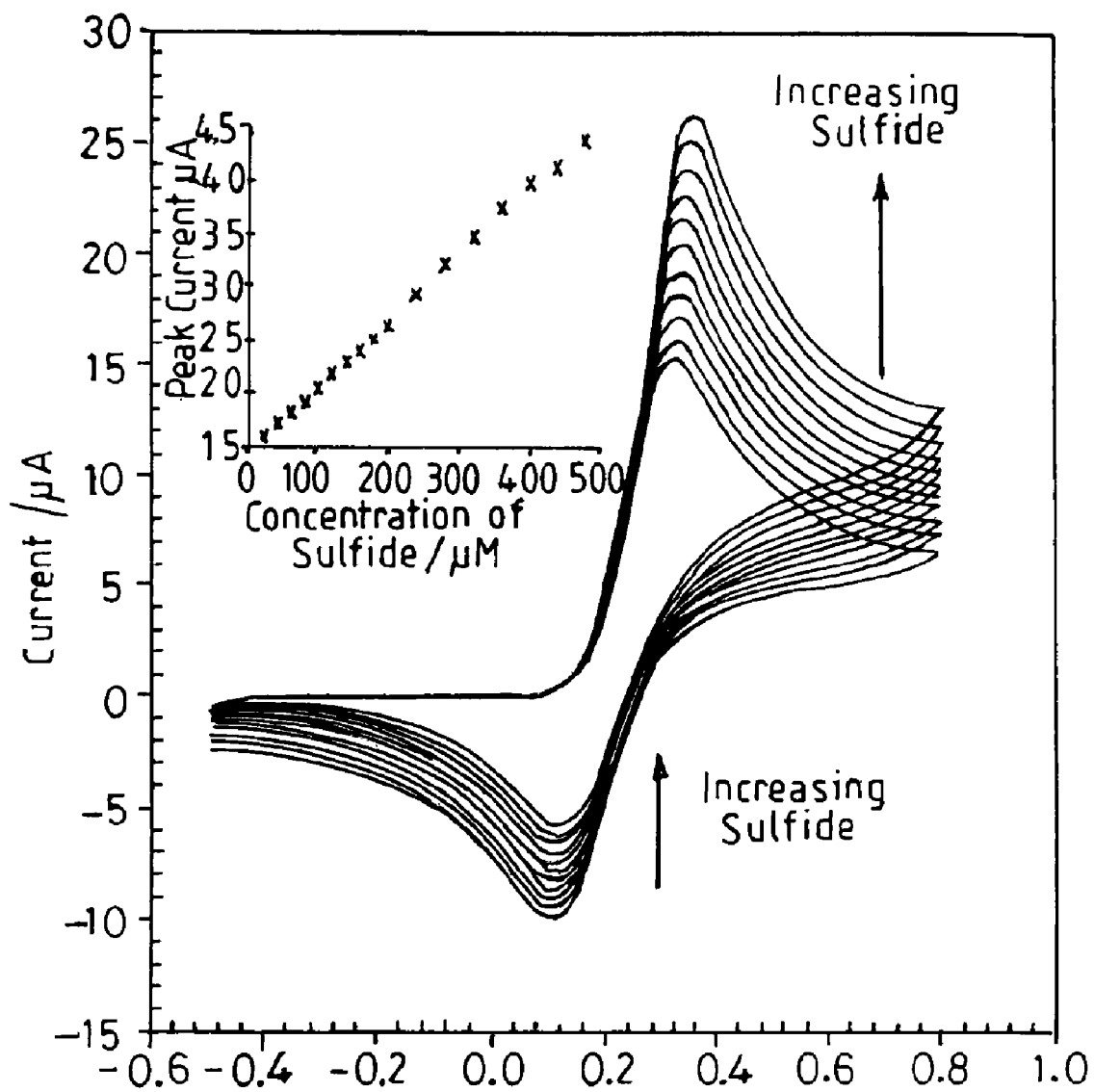
FIG. 8 shows cyclic voltammograms for the sensor of FIGS. 2 and 3 for various concentrations of hydrogen sulphide, but using ferrocyanide.

In particular, reagents other than DMPD can be used. For example, for higher concentrations of hydrogen sulphide, an aqueous solution of ferrocyanide ions, e.g. potassium ferrocyanide, or an aqueous ferrocene solution can been used. Cyclic voltammograms for the sensor 30 using an aqueous solution of ferrocyanide ions are shown in FIG. 8, which again includes an inset graph showing the variation of the peak oxidation current with sulphide concentration.

Figure 9A:
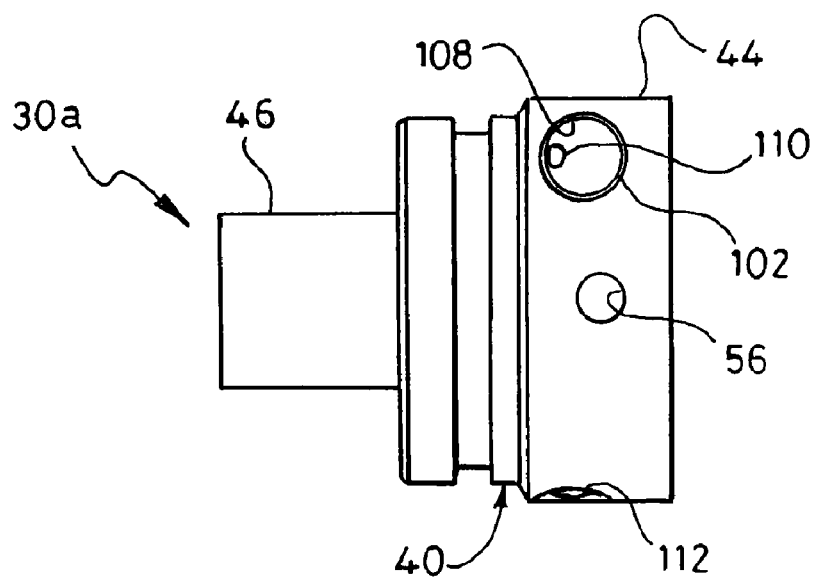
FIGS. 9A and 9B show a modified version of the sensor of FIGS. 2 and 3, incorporating a pressure balancing feature.
Figure 9B:
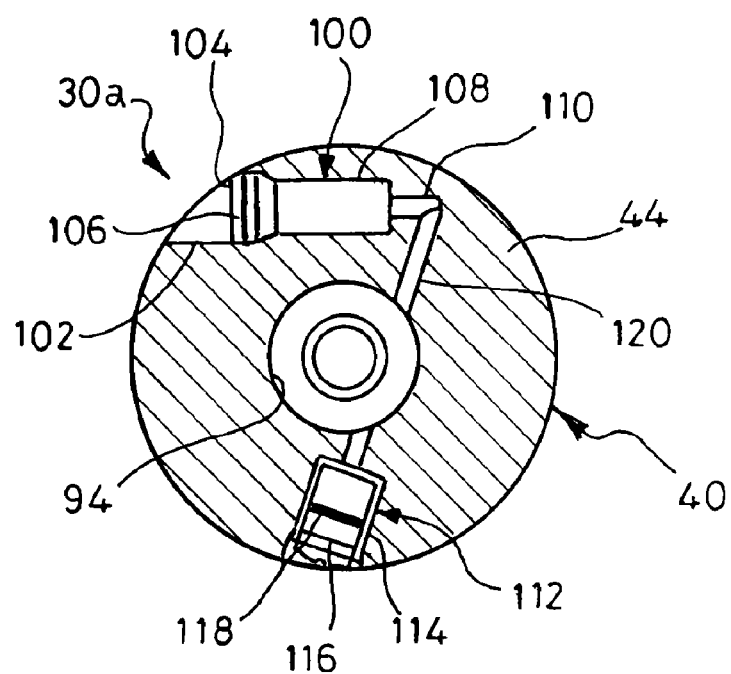

To further improve the high pressure capability of the sensor 30, the pressures on both sides of the membrane 82 can be balanced, as achieved in the modified version of the sensor 30 indicated at 30a in FIGS. 9A and 9B. The sensor 30a is substantially identical to the sensor 30 except for the addition of the pressure balancing feature, so corresponding elements have the same reference numbers, and only the differences, due to the pressure balancing feature, will be described.

In the sensor 30a, the upper portion 44 of the housing 40 has a first cylindrical bore 100 drilled into it parallel to but partly below the flowpath 56 and offset from the chamber 94, the bore having an initial larger diameter portion 102 containing a movable piston 104 sealed in the bore by a VITON™ O-ring 106. The bore 100 continues with a coaxially aligned intermediate diameter portion 108, and finishes in a small diameter duct portion 110 aligned with the bottom of the intermediate diameter portion and at the level of chamber 94.

A second cylindrical bore 112 is drilled into the upper portion 44 of the housing 40 at an angle of about 70 degrees to the first bore 100, this second bore having an initial larger diameter portion 114 containing a piston-like plug member 116 sealed in the bore by a VITON™ O-ring 118 substantially equal in length to the larger diameter portion 114. The bore 112 finishes in a small diameter duct portion 120 aligned with the bottom of the portion 114 of the bore and at the level of the chamber 94, this passage forming a chord through one side of the circular cross-section of the chamber 94 and intercepting the end of the passage 110.

It will therefore be appreciated that the respective portions of the bores 100 and 112 disposed between the piston 104 and the piston-like plug member 116 effectively form extensions to the chamber 94, so that in use the liquid reagents in the chamber also fill these portions of the bores. Additionally, the respective surfaces of the piston 104 and the plug-like piston member 116 facing out of the bores 100 and 112, being above the level of the sealing ring in the groove 96 in the upper portion 44 of the housing 40 of the sensor 30a, are effectively exposed to the pressure of the hydrocarbons in the flowpath 56. The piston 104 therefore maintains the pressure of the liquid reagents in the chamber 94 substantially equal to the pressure of the hydrocarbons in the flowpath 56, thus substantially eliminating the pressure differential across the membrane 82 and prolonging its useful life. The piston-like plug member 116, to the extent that it is capable of very slight movement in response to pressure, assists in the pressure balancing function of the piston 104, while the respective portions of the bores 100 and 112 disposed between the piston 104 and the piston-like plug member 116 effectively increase the volume or capacity of the chamber 94 and therefore increase the volume of the reagents available in the sensor 30a.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A wellbore tool comprising an electrochemical sensor for measuring the amount of hydrogen sulphide or thiols in a fluid, the sensor comprising:
a housing having a flow path for the fluid therethrough,
a gas permeable membrane disposed in the housing and having one side exposed to the flow path,
a chamber disposed in the housing, the chamber being exposed to the other side of the membrane and containing reagents which together with the hydrogen sulphide or thiols entering the chamber via the membrane create a redox reaction resulting in an electrical current dependent upon the amount of hydrogen sulphide or thiols in said fluid, and
at least two electrodes in the chamber which is exposed to the other side of the membrane, said electrodes being a working electrode and a counter electrode spaced from each other and both exposed to the reagents in the chamber, the well bore tool also comprising
means for drawing in fluid and passing it along the said flow path, and
electronic circuitry connected to the electrodes in the chamber, operable to apply repeatedly varying potential to the working electrode and measure the peak current flowing between the working electrode and the counter electrode.

2. The wellbore tool of claim 1 wherein the housing is provided with pressure balancing means for reducing the difference between the respective pressures on each side of the membrane.

3. The electrochemical sensor as claimed in claim 2 wherein the pressure balancing means comprises a movable piston having a first pressure surface in pressure communication with the flow path and a second pressure surface in pressure communication with the chamber.

4. The wellbore tool of claim 3 wherein the first pressure surface of the movable partition, piston or bellow is directly exposed to the fluid, and the second pressure surface of the movable piston is directly exposed to the reagents.

5. The wellbore tool of claim 1 wherein the membrane is trapped between respective sealing means which extend around the periphery of the membrane on each side thereof.

6. The wellbore tool of claim 1 wherein said housing includes a first housing member which is generally cup-shaped and is provided with a centrally disposed aperture in its base, and a second housing member which fits into the cup-shaped first housing member so as to trap the membrane between the end of the second housing member within the first housing member and the base of the cup shape of the first housing member, said other side of the membrane completely covering said aperture, and the flow path extending transversely through both housing members and communicating with said one side of the membrane via a coaxially disposed conduit in the second housing member.

7. The wellbore tool of claim 6 wherein the housing includes a third housing member having a generally cylindrical recess for coaxially receiving the first and second housing members so as to define therewith a cylindrical space between the base of the cup shape of the first housing member and the base of the recess, said cylindrical space forming at least part of the chamber.

8. The wellbore tool of claim 6 wherein the sealing means on said other side of the membrane comprises a substantially coaxially disposed O-ring trapped between said other side of the membrane and the base of the cup shape of the first housing member, while the sealing means on the one side of the membrane comprises sealing engagement between said one side of the membrane and a planar surface formed on the end of the second housing member within the first housing member.

9. The wellbore tool of claim 8 wherein a further coaxially disposed O-ring is trapped between the base of the cup shape of the first housing member and the base of the recess.

10. The wellbore tool of claim 1 wherein said chamber includes a working electrode, a counter electrode and a reference electrode.

11. The wellbore tool of claim 10 wherein the electrodes are spaced apart in the chamber and arranged such that said current flows between the working and counter electrodes.

12. The wellbore tool of claim 11 wherein the working electrode is made from boron-doped diamond.

13. The wellbore tool of claim 11 wherein the working electrode is made from glassy carbon.

14. The wellbore tool of claim 11 wherein the working electrode is made from platinum.

15. The wellbore tool of claim 11 wherein the counter electrode is made of platinum.

16. The wellbore tool of claim 10 wherein the reference electrode is made of silver coated with silver chloride or silver iodide, or platinum.

17. The wellbore tool of claim 10, wherein the electrodes are mounted on or in an insulating base made from polyetheretherketone.

18. The wellbore tool of claim 6 wherein the housing members are made from polyetheretherketone.

19. The wellbore tool of claim 1 wherein the reagents include a phenylenediamine.

20. The wellbore tool of claim 1 wherein the reagents include an aqueous ferrocyanide or ferrocene solution.

21. The wellbore tool of claim 1 wherein the membrane is made from zeolite or a ceramic material.

22. The wellbore tool of claim 1 wherein the wellbore tool is provided with a sampling probe, said sampling probe being located at a distance comprised between 8 and 30 cm from said electrochemical sensor.

23. A method of measuring the amount of hydrogen sulphide or thiols in formation fluid from an earth formation surrounding a wellbore, the method comprising positioning a downhole tool in the wellbore adjacent to the formation, where said tool comprises an electrochemical sensor which comprises:
a housing having a flow path for the fluid therethrough,
a substantially rigid gas permeable membrane disposed in the housing and having one side exposed to the flow path,
a chamber disposed in the housing, the chamber being exposed to the other side of the membrane and containing reagents which together with the hydrogen sulphide or thiols entering the chamber via the membrane create a redox reaction resulting in an electrical current dependent upon the amount of hydrogen sulphide or thiols in said fluid, and
at least two electrodes in the chamber which is exposed to the other side of the membrane, said electrodes being a working electrode and a counter electrode spaced from each other and both exposed to the reagents in the chamber, passing formation fluid along the flow path, and repeatedly applying varying potential to the working electrode and measuring the peak current flowing between the working electrode and the counter electrode.

24. The method of claim 23 wherein said chamber includes a working electrode, a counter electrode and a reference electrode spaced apart in the chamber and arranged such that current flows between the working and counter electrodes.

25. The method of claim 24 wherein the working electrode is made from boron-doped diamond.

26. The method of claim 24 wherein the working electrode is made from glassy carbon.

27. A wellbore tool comprising an electrochemical sensor for measuring the amount of hydrogen sulphide or thiols in a fluid, the sensor comprising:
    a housing having a flow path for the fluid therethrough,
    a gas permeable membrane disposed in the housing and having one side exposed to the flow path,
    a chamber disposed in the housing, the chamber being exposed to the other side of the membrane and containing reagents which together with the hydrogen sulphide or thiols entering the chamber via the membrane create a redox reaction resulting in an electrical current dependent upon the amount of hydrogen sulphide or thiols in said fluid,
    wherein the housing is provided with pressure balancing means for reducing the difference between the respective pressures on each side of the membrane, and
    at least two electrodes in the chamber which is exposed to the other side of the membrane, said electrodes being a working electrode and a counter electrode spaced from each other and both exposed to the reagents in the chamber, the well bore tool also comprising means for drawing in fluid and passing it along the said flow path, and electronic circuitry connected to the electrodes in the chamber, operable to apply repeatedly varying potential to the working electrode and measure the peak current flowing between the working electrode and the counter electrode.

28. A wellbore tool comprising an electrochemical sensor for measuring the amount of hydrogen sulphide or thiols in a fluid, the sensor comprising:
    a housing having a flow path for the fluid therethrough,
    a gas permeable membrane disposed in the housing and having one side exposed to the flow path,
    a chamber disposed in the housing, the chamber being exposed to the other side of the membrane and containing an aqueous ferrocene solution which together with the hydrogen sulphide or thiols entering the chamber via the membrane create a redox reaction resulting in an electrical current dependent upon the amount of hydrogen sulphide or thiols in said fluid, and
    at least two electrodes in the chamber which is exposed to the other side of the membrane, said electrodes being a working electrode and a counter electrode spaced from each other and both exposed to the reagents in the chamber, the well bore tool also comprising means for drawing in fluid and passing it along the said flow path, and electronic circuitry connected to the electrodes in the chamber, operable to apply repeatedly varying potential to the working electrode and measure the peak current flowing between the working electrode and the counter electrode.

* * * * *